United States Patent
Overaker

(10) Patent No.: US 7,104,999 B2
(45) Date of Patent: Sep. 12, 2006

(54) SURGICAL ANCHOR INSERTER

(75) Inventor: David W. Overaker, Annandale, NJ (US)

(73) Assignee: Ethicon, Inc., Somerville, NJ (US)

( * ) Notice: Subject to any disclaimer, the term of this patent is extended or adjusted under 35 U.S.C. 154(b) by 344 days.

(21) Appl. No.: 10/609,336

(22) Filed: Jun. 28, 2003

(65) Prior Publication Data

US 2004/0267278 A1    Dec. 30, 2004

(51) Int. Cl.
*A61B 17/128* (2006.01)

(52) U.S. Cl. ...................... 606/142; 606/104
(58) Field of Classification Search .......... 606/104, 606/142, 232, 99
See application file for complete search history.

(56) References Cited

U.S. PATENT DOCUMENTS

| | | |
|---|---|---|
| 4,632,100 A | 12/1986 | Somers et al. |
| 4,870,957 A | 10/1989 | Goble et al. |
| 5,156,616 A | 10/1992 | Meadows et al. |
| 5,207,679 A | 5/1993 | Li |
| 5,217,486 A | 6/1993 | Rice et al. |
| 5,268,001 A | 12/1993 | Nicholson et al. |
| 5,395,372 A | 3/1995 | Holt et al. |
| 5,411,523 A | 5/1995 | Goble |
| 5,507,801 A | 4/1996 | Gisin et al. |
| 5,584,860 A | 12/1996 | Goble et al. |
| 5,662,658 A | 9/1997 | Wenstrom, Jr. |
| 5,725,529 A | 3/1998 | Nicholson et al. |
| 5,814,072 A | 9/1998 | Bonutti |
| 5,868,789 A | 2/1999 | Huebner |
| 5,935,129 A | 8/1999 | McDevitt et al. |
| 5,948,001 A | 9/1999 | Larsen |
| 5,948,002 A | 9/1999 | Bonutti |
| 5,968,044 A | 10/1999 | Nicholson et al. |
| 5,993,463 A | 11/1999 | Truwit |
| 5,997,552 A * | 12/1999 | Person et al. ............... 606/139 |
| 6,033,430 A | 3/2000 | Bonutti |
| 6,136,001 A | 10/2000 | Michelson |
| 6,136,032 A | 10/2000 | Viladot Perice et al. |
| 6,312,448 B1 | 11/2001 | Bonutti |
| 6,554,852 B1 | 4/2003 | Oberlander |
| 2002/0143329 A1 | 10/2002 | Serhan et al. |

FOREIGN PATENT DOCUMENTS

| | | |
|---|---|---|
| WO | WO 97/29693 | 8/1997 |
| WO | WO 01/06909 A2 | 2/2001 |

OTHER PUBLICATIONS

U.S. Appl. No. 10/112,619, "Expandable Cable Anchor", Filed Mar. 29, 2002.
U.S. Appl. No. 10/112,618, "Threaded Cable Anchor", Filed Mar. 29, 2002.

* cited by examiner

*Primary Examiner*—Eduardo C. Robert
*Assistant Examiner*—D. Jacob Davis

(57) ABSTRACT

A surgical anchor inserter is equipped to receive or hold two or more bone anchors or the like. A corresponding number of ejection mechanisms can be actuated in concert to simultaneously deploy the anchors.

16 Claims, 7 Drawing Sheets

SURGICAL ANCHOR INSERTER

FIELD OF THE INVENTION

The present invention relates to surgical instruments, and, more specifically, to an inserter for simultaneously deploying a plurality of anchors to secure a surgical construct to bone.

BACKGROUND OF THE INVENTION

Single level spine fusion procedures typically entail removing the intervertebral disk and inserting an interbody device into the disk space. Current spine fusion procedures rely heavily on the use of posterior fixation to achieve the stability and rigidity necessary to obtain successful clinical results. However, implantation of posterior instrumentation necessarily involves removing important musculoskeletal elements. Because of these concerns, anterior fixation systems have also been developed which require removal of much less musculoskeletal mass. However, because anterior fixation, especially in the abdominal or thoracic area, lies in close proximity to vital internal organs (e.g., the aorta), these fixation systems must also possess a low profile.

In general, conventional intervertebral connection systems can be characterized by ligament components that are either: (1) relatively rigid; or (2) not shaped for cooperative connection to bone anchors; or (3) by bone anchors that are shouldered to seat upon the vertebral surface. When the ligament is relatively rigid, it must essentially lie fully upon the anterior surfaces of the adjacent vertebrae, thereby limiting design options. Systems having relatively rigid ligaments typically have transverse holes near their end portions for accepting bone anchors. In systems in which the ligament is not shaped for cooperative attachment to the bone anchor, attachment is typically made by either suturing or by passing a screw through the ligament. When the bone anchor is seated upon the vertebral surface, a portion of the bone anchor protrudes from the surface and the tension of the ligament cannot be further adjusted.

In commonly-owned U.S. patent application Ser. No. 09/822,126, entitled "Intervertebral Connection System", filed Mar. 30, 2001, and incorporated herein by reference, there is disclosed an intervertebral connection system comprising a ligament having a central portion, first and second end portions, first and second conformable portions, and first and second shoulderless bone anchors (see U.S. Patent Publication No. US2002/0143329 A1, dated Oct. 3, 2002, which publication is also incorporated herein by reference). The shoulderless feature of the bone anchor allows the bone anchor to be fully driven into the vertebral surface, thereby eliminating any problematic protrusion while also providing a means to adjust the tension of the ligament after the bone anchors have been located. The conformable portions of the ligament allow the ligament to conform to the recess produced by a fully driven bone fastener without generating undue stress, thereby accommodating the surgeon's desire to fully drive the bone fastener within the recess. The cooperative shape of the ligament end portions allows for non-destructive attachment of the ligament to the bone anchors without the use of sutures, thereby minimizing unwanted connection-related stresses and undesirable generation of foreign particles within the patient.

In commonly-owned U.S. patent application Ser. No. 10/112,619, entitled "Expandable Cable Anchor", filed Mar. 29, 2002, and incorporated herein by reference, there is disclosed a bone anchoring device for securing suture or cable within a bone hole. The bone anchoring device includes a radially expandable sheath, an expander member for expanding the sheath, and a washer. As disclosed in the application, two bone anchoring devices could be connected via a cable and used to hold a bone block between adjacent vertebrae in spinal fusion procedures.

Bone anchors for attaching soft tissue or sutures to bone are well known in the art. Also well known in the art are inserter tools for deploying such bone anchors in a hole in bone tissue. All of the known art describes deployment of a single anchor to secure a structure to bone.

In the case of multiple anchor surgical constructs, such as the intervertebral connection system described above, there is a need for an inserter that can simultaneously deploy a plurality of bone anchors. More specifically, an inserter is needed wherein a surgical construct, comprising two or more anchors connected by a ligament or cable, can be readily assembled to the inserter for delivery and simultaneous deployment of the anchors into holes in bone.

SUMMARY OF THE INVENTION

The problems and disadvantages of the prior art devices described above are overcome in accordance with the present invention by providing a new and improved surgical anchor inserter which is specifically adapted to simultaneously deploy multiple surgical anchors. More particularly, the new and improved inserter includes at least a pair of receiving mechanisms or means, each of which can be in the form of a receptacle such as a cannulated sleeve sized and shaped so as to accommodate a surgical anchor therein. The inserter also includes at least a pair of ejecting mechanisms or means, one for each of the receiving means. Each of the ejecting means can be in the form of a,cannulated pin which functions to eject a surgical anchor from an associated receiving means in response to relative movement between the associated receiving means and its corresponding ejecting means. All of the ejecting means can be activated by a single actuating mechanism or means, such as a manually grippable handle which initiates the movement of the ejecting means relative to the receiving means.

BRIEF DESCRIPTION OF THE DRAWINGS

For a better understanding of the present invention, reference is made to the following detailed description of an exemplary embodiment considered in conjunction with the accompanying drawings, in which.

DETAILED DESCRIPTION OF THE EXEMPLARY EMBODIMENT

Figure 1:
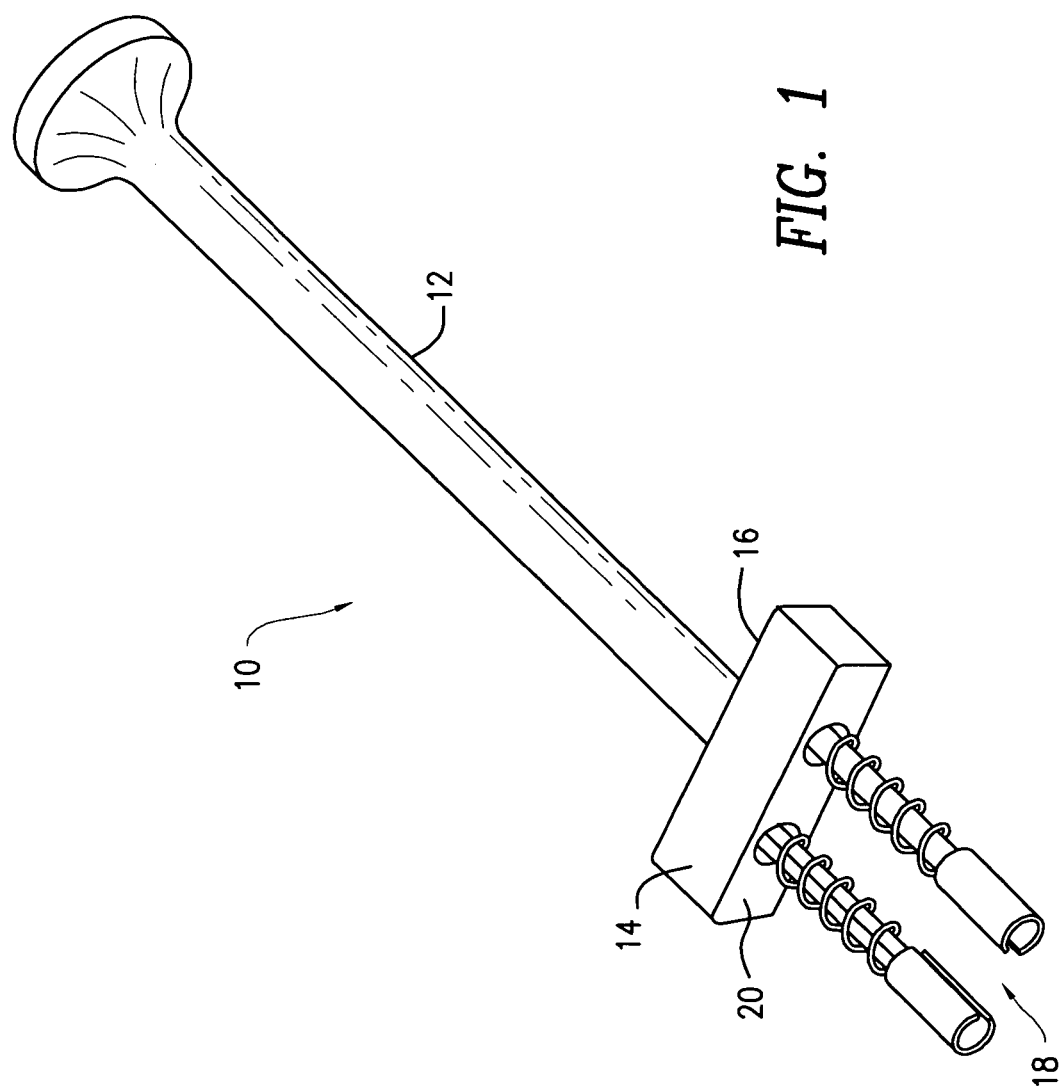
FIG. 1 is a perspective view of a dual anchor inserter constructed in accordance with one exemplary embodiment of the present invention.
Figure 2:
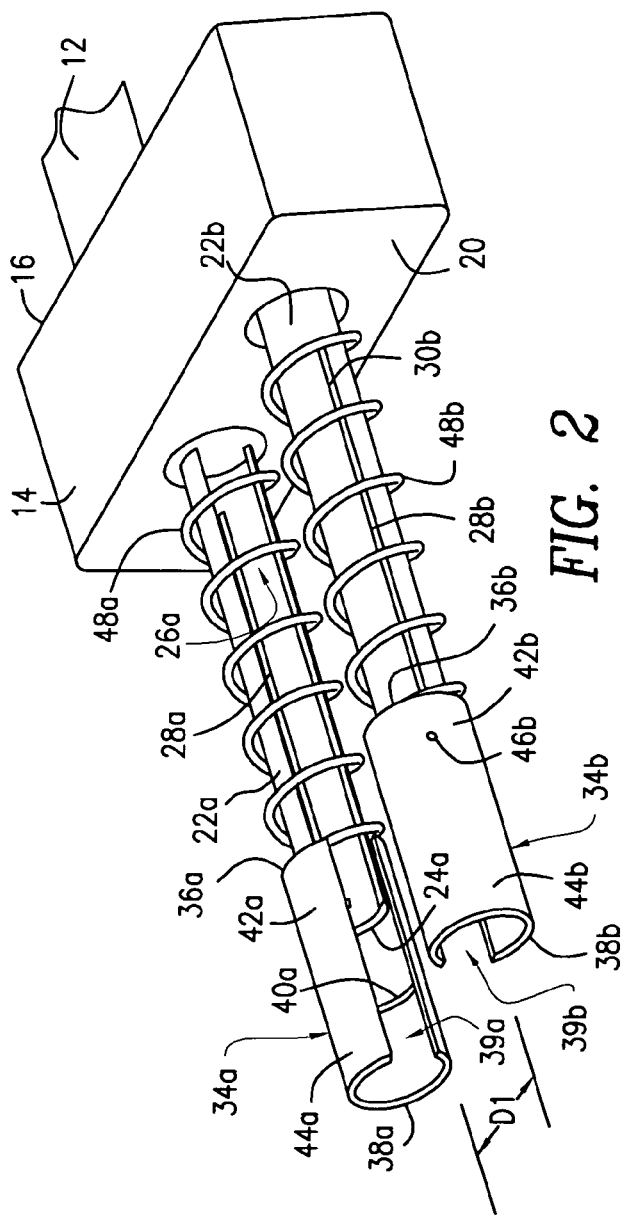
FIG. 2 is a perspective view of the distal end of the dual anchor inserter depicted in FIG. 1.
Figure 3:
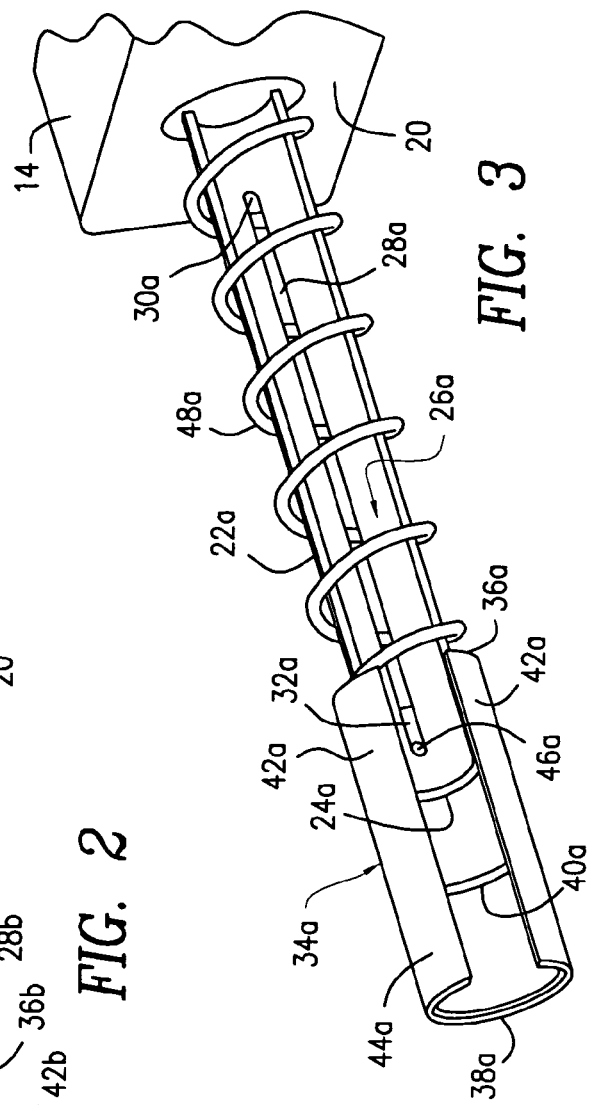
FIG. 3 is a perspective view of the right leg of the dual anchor inserter depicted in FIGS. 1 and 2.

Referring initially to FIGS. 1–3, there is shown a dual anchor inserter 10 for use in anchoring a dual anchor surgical construct to bones of an affected patient. The inserter 10 includes a handle 12, which is sized and shaped so as be grippable by the hand of a surgeon, and a head 14, which is immovably attached on one side 16 thereof to the handle 12, whereby the handle 12 and the head 14 move conjointly. A dual anchor deployment assembly 18 is attached to an opposite side 20 of the head 14.

Figure 6:
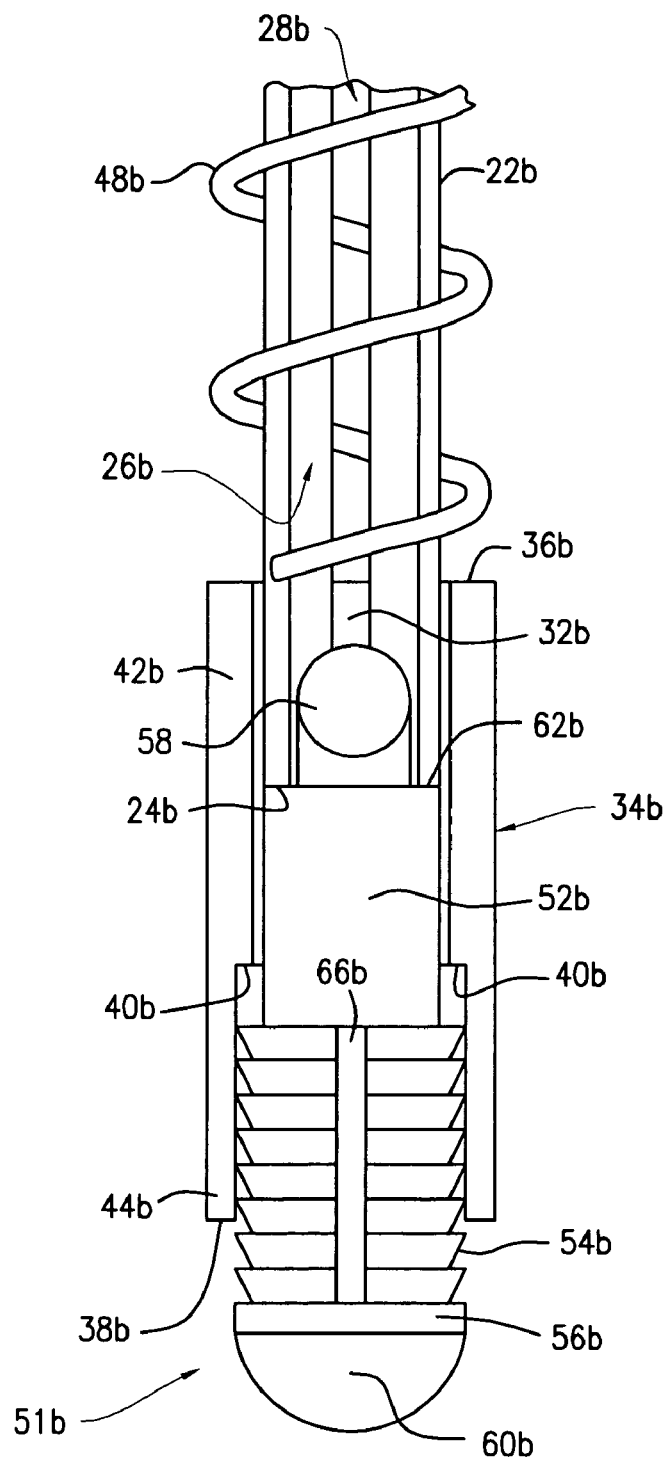
FIG. 6 is a partial cross-sectional view of the left leg of the assembly depicted in FIG. 5.

With particular reference to FIGS. 2 and 3, the dual anchor deployment assembly 18 includes a pair of essentially identical pins 22a, 22b, each of which extends from the head 14 to a free or distal end 24a, 24b, respectively (see FIGS. 3 and 6). Both of the pins 22a, 22b are cannulated and generally cylindrical in shape. More particularly, each pin 22a, 22b includes a cutout 26a, 26b, respectively (see FIGS. 3 and 6), whereby each of the pins 22a, 22b has a generally C-shaped lateral cross section. The pins 22a, 22b are releaseably or permanently attached to the head 14 such that they extend in parallel fashion at a spaced apart distance D1 with their cutouts 26a, 26b facing each other. The opposite (i.e., outer) sides of the pins 22a, 22b are provided with longitudinally extending slots 28a, 28b, respectively. Each of the slots 28a, 28b has a proximal end 30a, 30b, respectively, and a distal end 32a, 32b, respectively (see FIGS. 2, 3 and 6).

Still referring to FIGS. 2 and 3, the dual anchor deployment assembly 18 also includes a pair of essentially identical cylindrical sleeves 34a, 34b, each of which is coaxially mounted on a corresponding one of the pins 22a, 22b, respectively, for reciprocating movement relative thereto. Each of the sleeves 34a, 34b includes a proximal end 36a, 36b, respectively, and a distal end 38a, 38b, respectively. Like the pins 22a, 22b, the sleeves 34a, 34b have cutouts 39a, 39b, respectively, thereby providing each of the sleeves 34a, 34b with a generally C-shaped lateral cross section.

Focusing initially on the sleeve 34a, it also includes an inner annular shoulder 40a positioned intermediate its proximal and distal ends 36a, 38a, thereby dividing the sleeve 34a into a small diameter portion 42a and a large diameter portion 44a. The inner diameter of the small diameter portion 42a is slightly larger than the outer diameter of the pin 22a, thereby allowing the sleeve 34a to slide or otherwise move back and forth over the free end 24a of the pin 22a. A peg 46a (see FIG. 3) extends radially into the small diameter portion 42a of the sleeve 34a. When the sleeve 34a is mounted on the pin 22a, the peg 46a is slidably received in the slot 28a of the pin 22a. A spring 48a is positioned between the side 20 of the head 14 and the proximal end 36a of the sleeve 34a such that the spring 48a urges the sleeve 34a into an extended position in which the peg 46a engages the distal end 32a of the slot 28a in the pin 22a, thereby preventing the ejection of the sleeve 34a from the pin 22a.

Turning now to the sleeve 34b, it further includes an inner annular shoulder 40b (see FIG. 6) positioned intermediate its proximal and distal ends 36b, 38b, thereby dividing the sleeve 34b into a small diameter portion 42b and a large diameter portion 44b. The inner diameter of the small diameter portion 42b is slightly larger than the outer diameter of the pin 22b, thereby allowing the sleeve 34b to slide or otherwise move back and forth over the free end 24b of the pin 22b (see FIG. 6). A peg 46b (FIG. 2) extends radially into the small diameter portion 42b of the sleeve 34b. When the sleeve 34b is mounted on the pin 22b, the peg 46b is slidably received in the slot 28b of the pin 22b. A spring 48b is positioned between the side 20 of the head 14 and the proximal end 36b of the sleeve 34b such that the spring 48b urges the sleeve 34b into an extended position in which the peg 46b engages the distal end 32b of the slot 20b in the pin 22b, thereby preventing the ejection of the sleeve 34b from the pin 22b.

Figure 4:
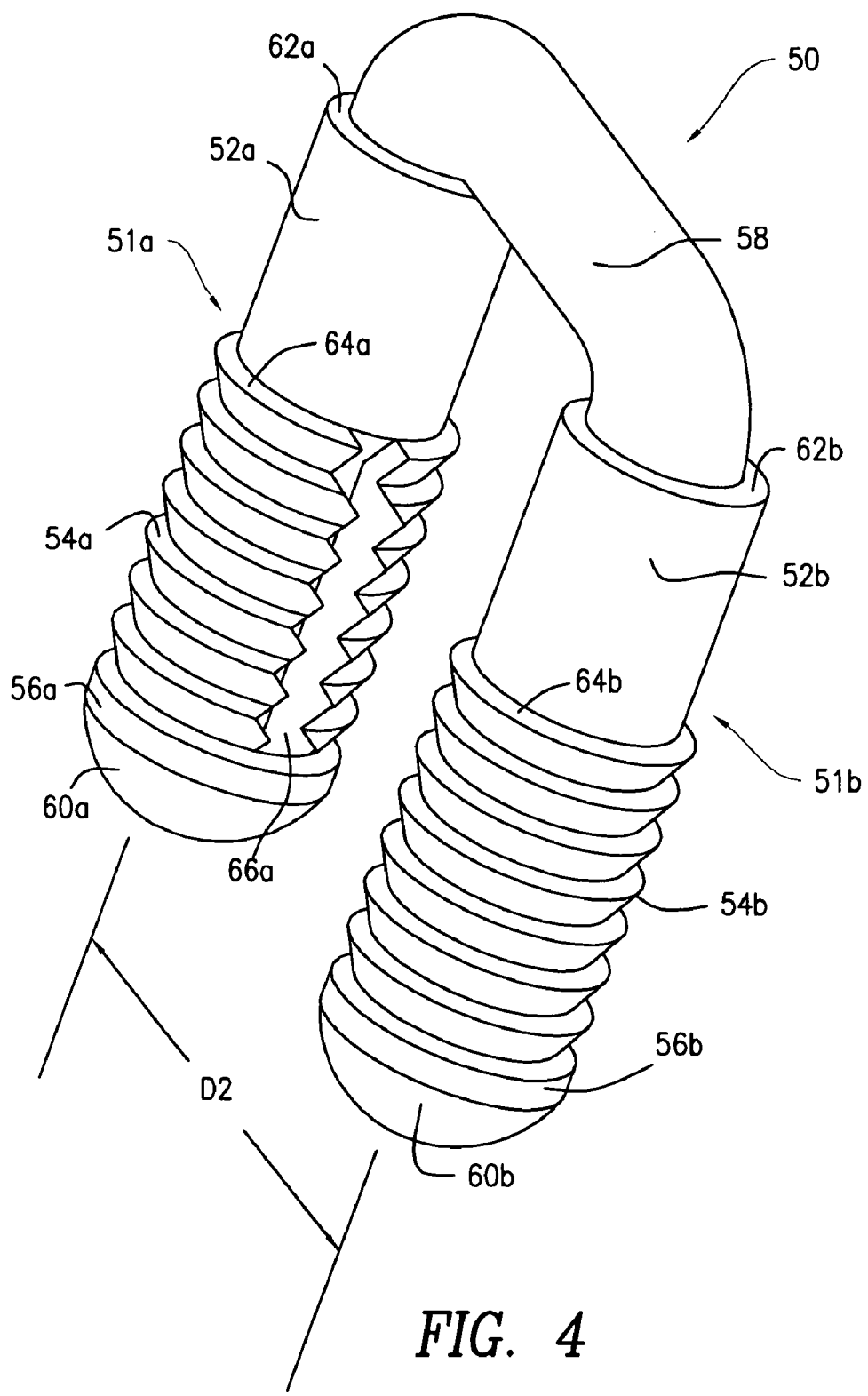
FIG. 4 is a perspective view of a dual anchor surgical construct adapted use with the dual anchor inserter of FIGS. 1–3.

With reference to FIG. 4, there is shown a dual anchor surgical construct 50, which is specifically adapted for use as an intervertebral connection system. More particularly, the surgical construct 50 includes a pair of anchor assemblies 51a, 51b comprising expanders 52a, 52b, respectively; sheaths 54a, 54b, respectively; and washers 56a, 56b, respectively. A cable 58, which has bending flexibility and axial stiffness, passes axially through the anchor assemblies 51a, 51b. The substantially U-shaped cable 58 terminates in a pair of enlarged, hemispherical tips 60a, 60b such that the expanders 52a, 52b, the sheaths 54a, 54b, and the washers 56a, 56b are irremovably mounted on the cable 58. The expanders 52a, 52b have proximal surfaces 62a, 62b, respectively, while the sheaths 54a, 54b have proximal surfaces 64a, 64b, respectively. The sheaths 54a, 54b also have longitudinal slots 66a, 66b, respectively (see FIGS. 4 and 6).

Figure 5:
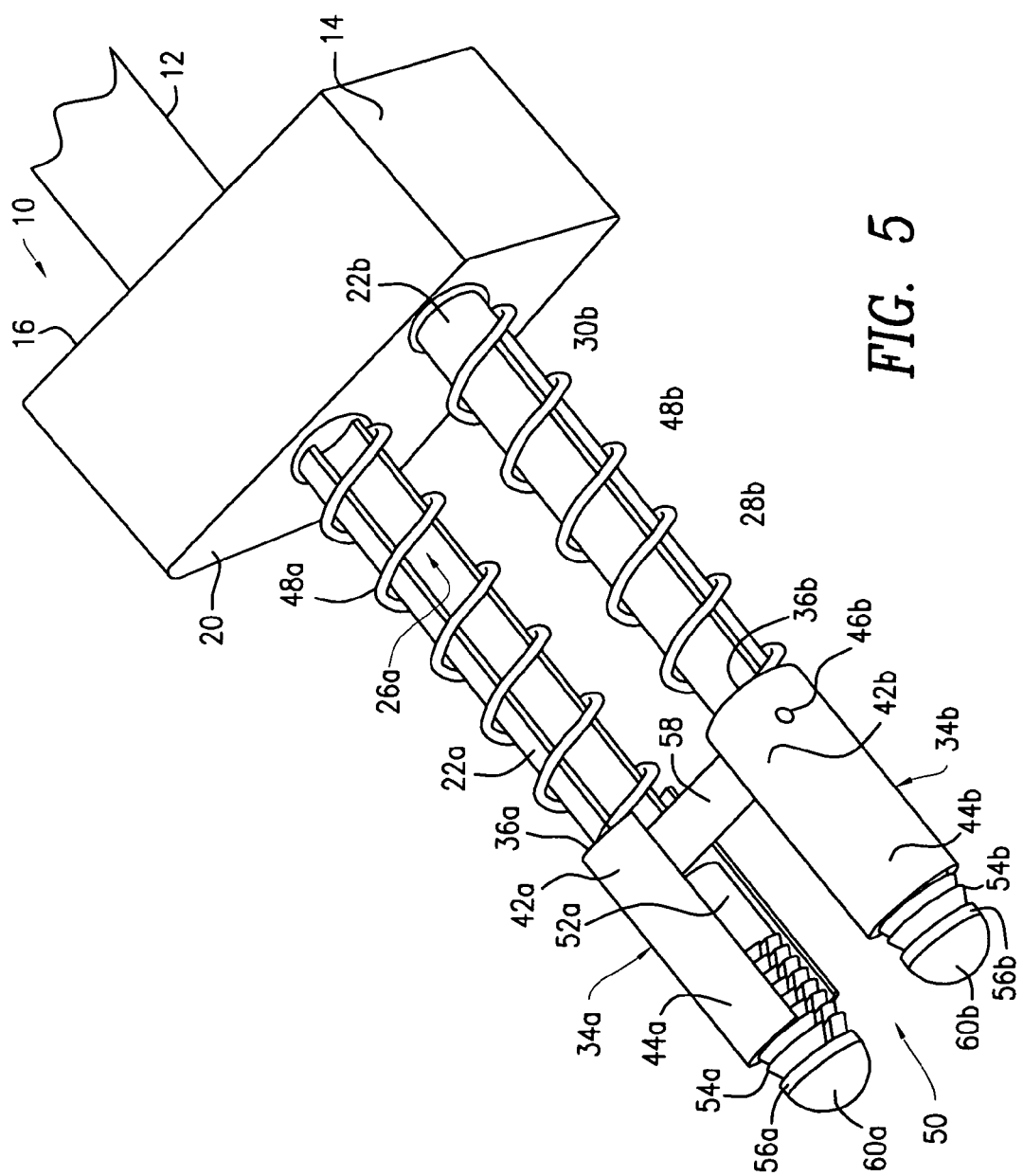
FIG. 5 is a perspective view showing the dual anchor inserter of FIGS. 1–3 in an assembled configuration with the surgical construct of FIG. 4.

Referring now to FIGS. 5 and 6, the dual anchor inserter 10 is shown assembled to the surgical construct 50 with both of the expanders 52a, 52b and both of the sheaths 54a, 54b inserted axially into the sleeves 34a, 34b, respectively. The inner diameter of the small diameter portions 42a, 42b of the sleeves 34a, 34b is slightly larger than the outer diameter of the expanders 52a, 52b so that the expanders 52a, 52b can be easily inserted into their respective sleeves 34a, 34b. The inner diameter of the large diameter portions 44a, 44b of the sleeves 34a, 34b is slightly smaller than the outermost diameter of the sheaths 54a, 54b such that an interference fit holds the sheaths 54a, 54b within their respective sleeves 34a, 34b. The surgical construct 50 is fully assembled to the dual anchor inserter 10 when the proximal surfaces 62a, 62b of the expanders 52a, 52b contact the free ends 24a, 24b of the pins 22a, 22b and the distance D2 (see FIG. 4) is equal to the distance D1 (see FIG. 2). When the surgical construct 50 is fully assembled to the dual anchor inserter 10, the cable tips 60a, 60b and adjacent portions of the sheaths 54a, 54b extend outwardly from their respective sleeves 34a, 34b (see FIG. 5).

The cutouts 39a, 39b in the sleeves 34a, 34b allow the cable 58 to span the distance D1 directly between the expanders 52a, 52b. The cutouts 26a, 26b allow the pins 22a, 22b to transmit load to the expanders 52a, 52b, respectively, via contact between the free ends 24a, 24b of the pins 22a, 22b and the proximal surfaces 62a, 62b of the expanders 52a, 52b, without interfering with the cable 58. The inner diameter of the pins 22a, 22b is at least equal to, or preferably slightly larger than, the diameter of the cable 58.

Figure 7:
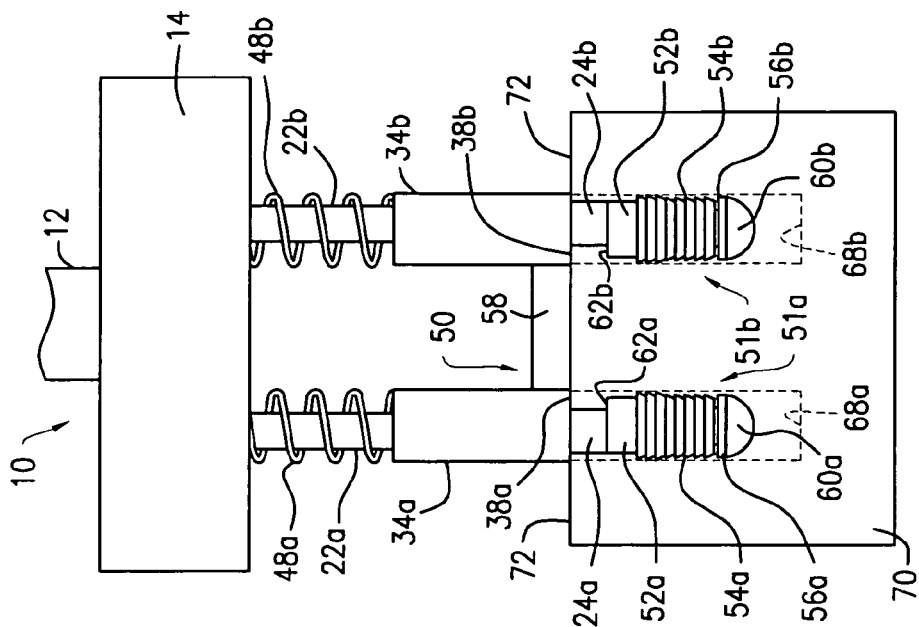
FIG. 7 is a side elevational view of the assembly depicted in FIG. 5 prior to its deployment in a pair of bone holes.
Figure 8:
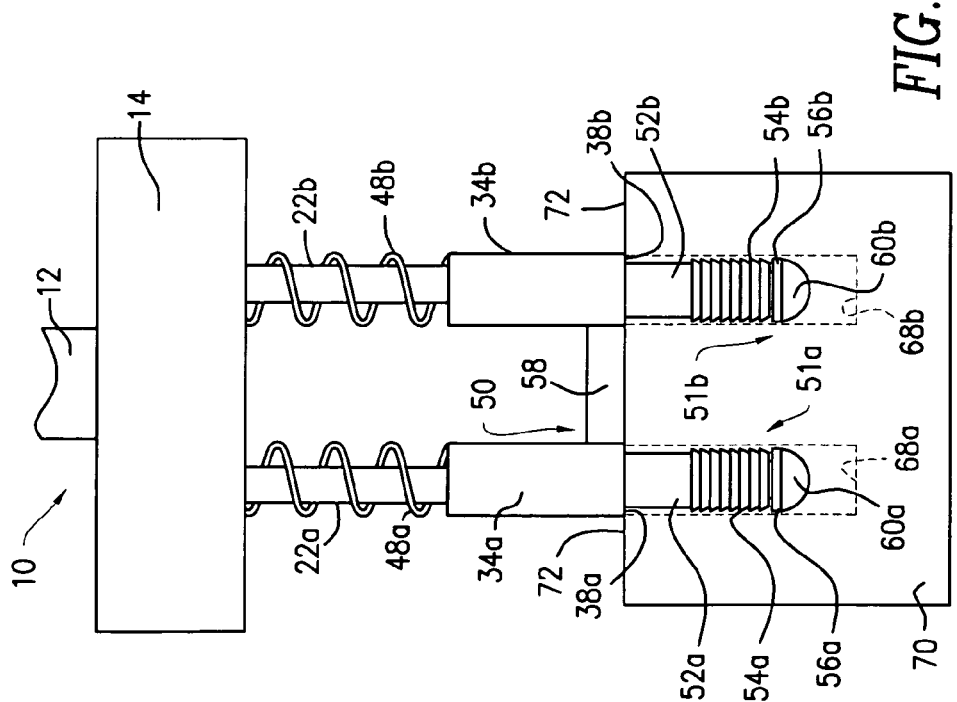
FIG. 8 is a side elevational view of the assembly depicted in FIG. 5 during its deployment in a pair of bone holes.
Figure 9:
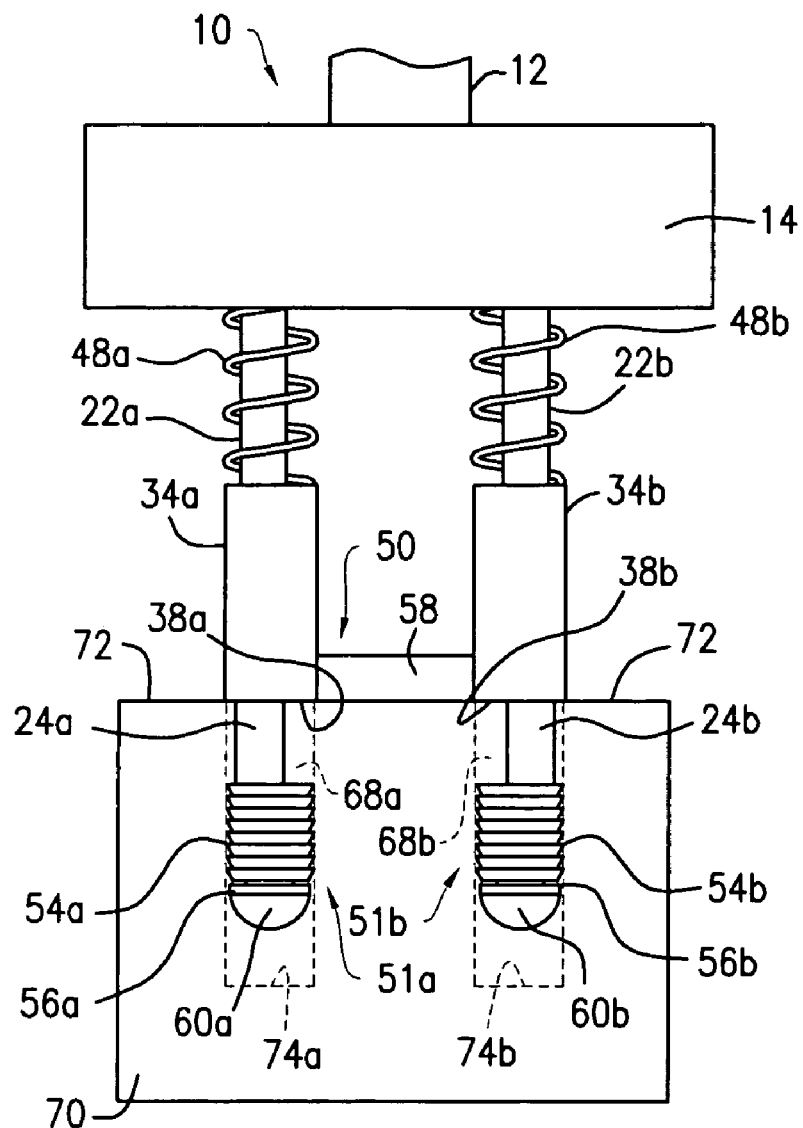
FIG. 9 is a side elevational view of the assembly depicted in FIG. 5 after it has been fully deployed in a pair of bone holes.

FIGS. 7–9 show the dual anchor inserter 10 in an assembled configuration with the surgical construct 50, when deployed in a pair of bone holes 68a, 68b in order to anchor the cable 58 in two locations in bone 70. Each of these figures will be described in greater detail hereinafter.

FIG. 7 shows the initial deployment configuration of the assembly, demonstrating the placement of the expanders 52a, 52b; the sheaths 54a, 54b; the washers 56a, 56b; and the cable 58 within the bone holes 68a, 68b. The diameter of the bone holes 68a, 68b is slightly larger than the outer diameter of the washers 56a, 56b. In general, the placement procedure involves aligning the longitudinal axes of the pins 22a, 22b with the bone holes 68a, 68b, respectively; guiding the cable tips 60a, 60b into the bone holes 68a, 68b, respectively; and then applying a downward force to the handle 12 to drive the anchor assemblies 51a, 51b down into the bone holes 68a, 68b, respectively. When the distal ends 38a, 38b of the sleeves 34a, 34b contact outer surface 72 of the bone 70, continued downward force on the handle 12 forces the sleeves 34a, 34b to slide along the pins 22a, 22b toward the head 14, thereby allowing the anchor assemblies 51a, 51b to fully enter the bone holes 68a, 68b below the bone surface 72.

Referring to FIG. 8, after the proximal surfaces 62a, 62b of the expanders 52a, 52b have been pushed below the bone surface 72, continued downward force on the handle 12 is resisted by tension in the cable 58. The resulting tension in cable 58 serves as the reaction force to hold the sheaths 54a, 54b as expanders 52a, 52b are driven by the pins 22a, 22b, respectively, into sheaths 54a, 54b with the continued application of downward force to the handle 12.

FIG. 9 shows the final configuration after deployment of the expanders 52a, 52b into the sheaths 54a, 54b, the proximal surfaces 62a, 62b of the expanders 52a, 52b now being flush with the proximal surfaces 64a, 64b of the sheaths 54a, 54b. In the fully deployed final configuration, interference between the expanders 52a, 52b and sheaths 54a, 54b forces the sheaths 54a, 54b to expand laterally, whereby the sheaths 54a, 54b engage walls 74a, 74b of the bone holes 68a, 68b with an interference fit. The outer diameter of the pins 22a, 22b must be slightly less than the diameter of bone holes 68a, 68b so that the pins 22a, 22b can travel within their respective bone holes 68a, 68b.

FIGS. 7–9 show the surgical construct 50 being deployed in a single bone 70. However, when used as an intervertebral connection system the surgical construct 50 would hold a bone block between adjacent vertebrae in spinal fusion procedures. In such cases, the two anchor assemblies 51a, 51b would be deployed in two different bones.

The embodiment described herein is merely exemplary and hence it is susceptible to variation and modification without departing from the scope of the present invention. All such variations and modifications are intended to be included within the scope of the invention as defined in the appended claims.

The invention claimed is:

1. An inserter for multiple surgical anchors, comprising first receiving means for receiving one of the surgical anchors, said first receiving means including a first cannulated sleeve which is sized and shaped so as to receive said one surgical anchor therein; first ejecting means for ejecting said one surgical anchor from said first receiving means, said first ejecting means including a first cannulated pin, said first cannulated sleeve being mounted on said first cannulated pin for reciprocating movement relative thereto; second receiving means for receiving another of the surgical anchors, said second receiving means including a second cannulated sleeve which is sized and shaped so as to receive said another surgical anchor therein; second ejecting means for ejecting said another surgical anchor from said second receiving means, said second ejecting means including a second cannulated pin, said second cannulated sleeve being mounted on said second cannulated pin for reciprocating movement relative thereto; and actuating means for simultaneously actuating said first and second ejecting means, whereby said one surgical anchor is ejected from said first receiving means while said another surgical anchor is being ejected from said second receiving means.

2. An inserter according to claim 1, wherein said first cannulated sleeve is mounted on a free end of said first cannulated pin and wherein said second cannulated sleeve is mounted on a free end of said second cannulated pin.

3. An inserter for multiple surgical anchors, comprising first receiving means for receiving one of the surgical anchors, said first receiving means including a first cannulated sleeve which is sized and shaped so as to receive said one surgical anchor therein; first ejecting means for ejecting said one surgical anchor from said first receiving means, said first ejecting means including a first cannulated pin, said first cannulated sleeve being mounted on a free end of said first cannulated pin for reciprocating movement relative thereto, said first cannulated sleeve is being movable between an extended position, in which said free end of said first cannulated pin is positioned within said first cannulated sleeve adjacent one end thereof, and a retracted position, in which said free end of said first cannulated pin extends outwardly from an opposite end of said first cannulated sleeve; second receiving means for receiving another of the surgical anchors, said second receiving means including a second cannulated sleeve which is sized and shaped so as to receive said another surgical anchor therein; second ejecting means for ejecting said another surgical anchor from said second receiving means, second ejecting means including a second cannulated pin, said second cannulated sleeve being mounted on a free end of said second cannulated pin for reciprocating movement relative thereto, said second cannulated sleeve being movable between an extended position, in which said free end of said second cannulated pin is positioned within said second cannulated sleeve adjacent one end thereof, and a retracted position, in which said free end of said second cannulated pin extends outwardly from an opposite end of said second cannulated sleeve; and actuating means for simultaneously actuating said first and second ejecting means, whereby said one surgical anchor is ejected from said first receiving means while said another surgical anchor is being ejected from said second receiving means.

4. An inserter according to claim 3, wherein said one surgical anchor is ejected from said first cannulated sleeve in response to the movement of said first cannulated sleeve from its said extended position to its said retracted position and wherein said another surgical anchor is ejected from said second cannulated sleeve in response to the movement of said second cannulated sleeve from its said extended position to its said retracted position.

5. An inserter according to claim 4, further comprising first urging means for urging said first cannulated sleeve into its said extended position and second urging means for urging said second cannulated sleeve into its said extended position.

6. An inserter according to claim 5, wherein said first urging means is a first spring and wherein said second urging means is a second spring.

7. An inserter according to claim 6, further comprising a head, said first and second cannulated pins extending outwardly from one side of said head in a spaced parallel relationship to one another.

8. An inserter according to claim 7, wherein said first spring is interposed between said one side of said head and said one end of said first cannulated sleeve and wherein said second spring is interposed between said one side of said head and said one end of said second cannulated sleeve.

9. An inserter according to claim 8, wherein said first cannulated sleeve includes a first peg which extends radially thereinto and wherein said second cannulated sleeve includes a second peg which extends radially thereinto.

10. An inserter according to claim 9, wherein said first cannulated pin includes a first slot extending longitudinally therealong, said first slot being sized and shaped so as to slidably receive said first peg, and wherein said second cannulated pin includes a second slot extending longitudinally therealong, said second slot being sized and shaped so as to slidably receive said second peg.

11. An inserter according to claim 10, wherein said first peg engages an end of said first slot when said first annulated sleeve is in its said extended position, thereby preventing said first spring from pushing said first cannulated sleeve off of said free end of said first cannulated pin, and wherein said second peg engages an end of said second slot when said second cannulated sleeve is in its said extended position, thereby preventing said second spring from pushing said second cannulated sleeve off of said free end of said second cannulated pin.

12. An inserter according to claim 11, wherein said actuating means includes a manually grippable handle extending outwarding from an opposite side of said head.

13. An inserter according to claim 12, wherein said handle, said head and said first and second cannulated pins are movable conjointly with each other.

14. An inserter according to claim 4, wherein said opposite end of said first cannulated sleeve has an inner diameter selected so as to create an interference fit with a sheath portion of said one surgical anchor and wherein said opposite end of said second cannulated sleeve has an inner diameter selected so as to create an interference fit with a sheath portion of said another surgical anchor.

15. An inserter according to claim 14, wherein said one surgical anchor includes an expander portion, which is movable into said sheath portion of said one surgical anchor for the expansion thereof, and wherein said another surgical anchor includes an expander portion which is movable into said sheath portion of said another surgical anchor for the expansion thereof.

16. An inserter according to claim 15, wherein said free end of said first cannulated pin is engageable with said expander portion of said one surgical anchor such that said free end of said first cannulated pin moves said expander portion of said one surgical anchor into said sheath portion of said one surgical anchor as said first cannulated sleeve moves towards its said retracted position, and wherein said free end of said second cannulated pin is engageable with said expander portion of said another surgical anchor such that said free end of said second cannulated pin moves said expander portion of said another surgical anchor into said sheath portion of said another surgical anchor as said second cannulated sleeve moves towards its said retracted position.

* * * * *

UNITED STATES PATENT AND TRADEMARK OFFICE
CERTIFICATE OF CORRECTION

| | | |
|---|---|---|
| PATENT NO. | : 7,104,999 B2 | Page 1 of 1 |
| APPLICATION NO. | : 10/609336 | |
| DATED | : September 12, 2006 | |
| INVENTOR(S) | : David W. Overaker | |

It is certified that error appears in the above-identified patent and that said Letters Patent is hereby corrected as shown below:

Column 7,
Line 13, replace "annulated" with -- cannulated --;

Column 7,
Line 24, replace "outwarding" with -- outwardly --;

Signed and Sealed this

Tenth Day of August, 2010

David J. Kappos
*Director of the United States Patent and Trademark Office*